(12) United States Patent
Chian

(10) Patent No.: US 6,929,622 B2
(45) Date of Patent: Aug. 16, 2005

(54) SAFETY SYRINGE CYLINDER

(76) Inventor: Lai-Wen Chian, 235 Chung-Ho Box 8-24, Taipei (TW)

( * ) Notice: Subject to any disclaimer, the term of this patent is extended or adjusted under 35 U.S.C. 154(b) by 294 days.

(21) Appl. No.: 10/194,514

(22) Filed: Jul. 15, 2002

(65) Prior Publication Data

US 2004/0010226 A1 Jan. 15, 2004

(51) Int. Cl.⁷ .................................. A61M 5/00
(52) U.S. Cl. .................. 604/110; 604/218; 604/198
(58) Field of Search ............... 604/198, 20, 96.4, 604/96.05; 606/3, 7, 10–17

(56) References Cited

U.S. PATENT DOCUMENTS 5,273,539 A * 12/1993 Chen .................... 604/110
5,885,257 A * 3/1999 Badger .................. 604/195
5,938,641 A * 8/1999 Villanueva ............. 604/195

* cited by examiner

Primary Examiner—Nicholas D. Lucchesi
Assistant Examiner—Cris L. Rodriguez

(57) ABSTRACT

A safety syringe cylinder has a structure for attaching a syringe needle precisely. The syringe needle can be retracted into the syringe cylinder for bending. A hook seat is formed at a lower end of the needle. An annular hook groove is formed at a top end of the push rod cap. The hook seat is engaged with the annular hook groove so as to control the displacement and bending process of the syringe needle. Thereby, the processing of undesired syringe needle is safe, reliable and convenient.

3 Claims, 7 Drawing Sheets

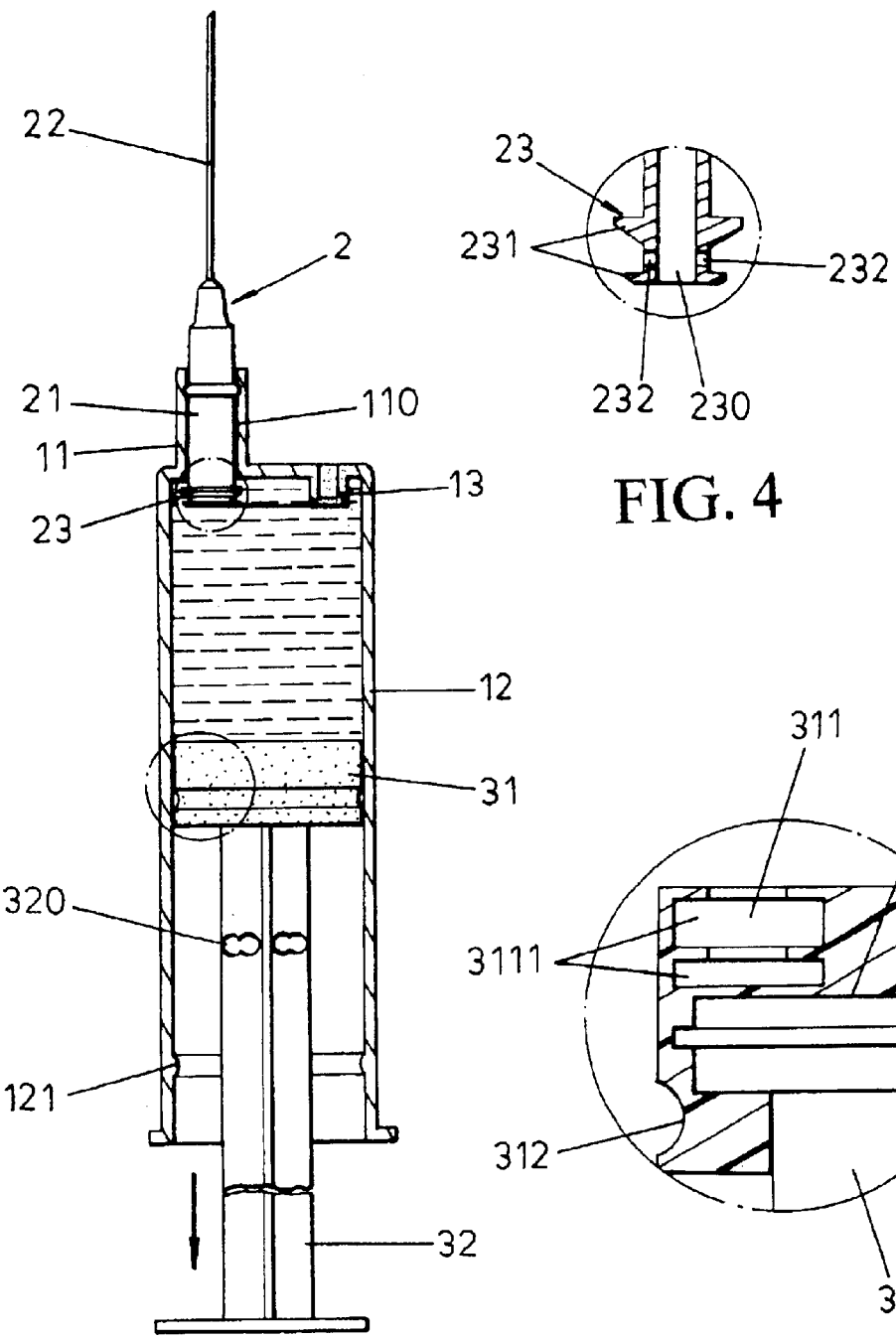
FIG. 4
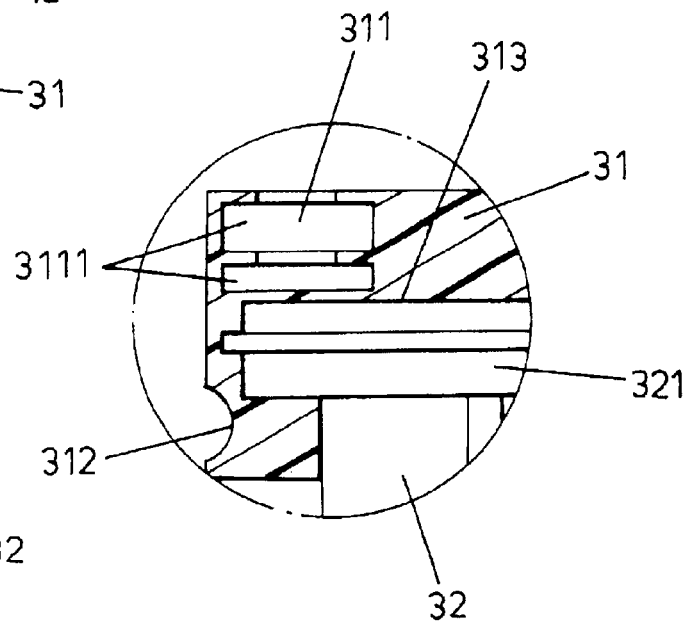
FIG. 5
FIG. 3

SAFETY SYRINGE CYLINDER

FIELD OF THE INVENTION

The present invention relates to medical devices, and particularly to a safety syringe cylinder having a structure for attaching a syringe needle precisely and the processing of undesired syringe needle is safe, reliable and convenient.

BACKGROUND OF THE INVENTION

Subcutaneous injections are frequently used in the medical treatment. Retractable safety syringe injectors are especially suitable for subcutaneous injection, which has the following advantages:

1. The retractable safety syringe cylinder is safe and retractable so as not to hurt anybody.
2. The retractable safety syringe cylinder has a self-destroy function. If an overlarge force is used to break the syringe cylinder, the needle will not be ejected out.
3. It is disposable after used once.
4. The use of the retractable safety syringe cylinder is similar to the conventional injector, it can be operated by a simple training.

FIG. 12 shows the structure of a retractable safety syringe cylinder. It contains a syringe cylinder 1, a syringe needle 2, a push rod 3, and others. The upper end of the syringe cylinder 1 has a syringe connecting seat 11 having a positioning hole 110 therein. The hole has a positioning groove 111 for retaining the syringe needle 2. The push rod 3 has a rod cap 30 which has a hook body 301. The needle of the syringe needle 2 has a slot 201. A periphery of the needle has a ring retained by the positioning groove 111, as shown in FIG. 11.

The use of the retractable safety syringe cylinder will be described herein. At first, the injector is checked. After injection, the hook body 301 can be inserted to the slot 201 correctly. The syringe needle 2 is exactly combined to the hook body 301 at a top of the push rod 3. When the push rod 3 is pulled backwards, the syringe needle 2 will retract into the syringe cylinder 1. When the push rod 3 is pressed again, the syringe needle 2 is bent and deformed in the syringe cylinder 1 so as to prevent from hurting anybody as it is deserted.

Although this retractable safety syringe cylinder has many advantages, when the push rod 3 is pulled backwards, the push rod 3 will rotate and thus the hook body 301 can not be inserted into the slot 201. Thus, the push rod 3 must be rotate again so that the hook body 301 and the hook groove 201 are engaged again. The operation is inconvenient.

SUMMARY OF THE INVENTION

Accordingly, the primary object of the present invention is to provide a safety syringe cylinder having a structure for attaching a syringe needle precisely. The syringe needle can be retracted into the syringe cylinder for bending. A hook seat is formed at a lower end of the needle. An annular hook groove is formed at a top end of the push rod cap. The hook seat is engaged with the annular hook groove so as to control the displacement and bending process of the syringe needle. Thereby, the processing of undesired syringe needle is safe, reliable and convenient.

The various objects and advantages of the present invention will be more readily understood from the following detailed description when read in conjunction with the appended drawing.

BRIEF DESCRIPTION OF THE DRAWINGS

FIG. 3 shows one embodiment of the present invention.

FIG. 4 is a partial structural view of the present invention.

FIG. 5 is a partial structural view of the present invention.

DETAILED DESCRIPTION OF THEE PREFERRED EMBODIMENTS

Figure 1:
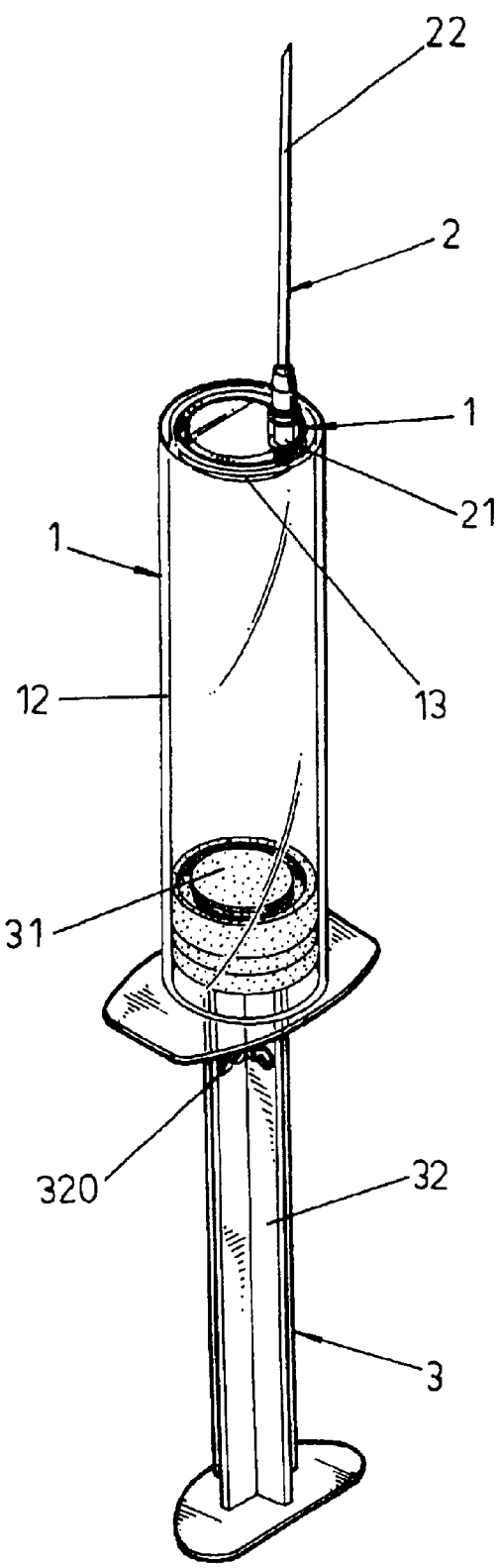
FIG. 1 is a structural schematic view of the present invention.
Figure 2:
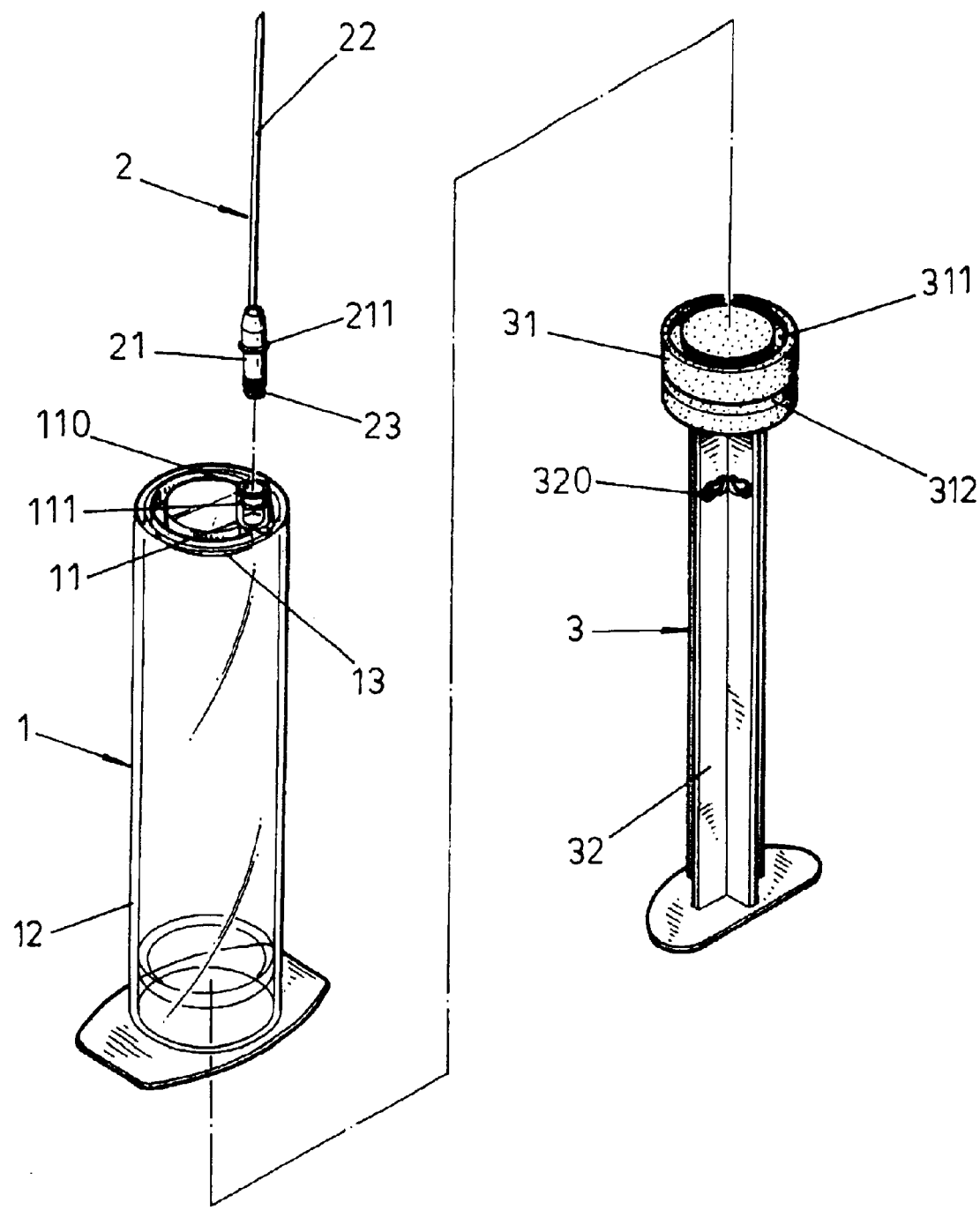
FIG. 2 is an exploded perspective view of the present invention.

Referring to FIGS. 1 and 2, the safety syringe cylinder of the present invention is illustrated. The safety syringe cylinder includes a syringe cylinder 1, a syringe needle 2, a push rod 3 and others.

The upper end of the syringe cylinder 1 has a syringe connecting seat 11. The syringe connecting seat 11 has a positioning groove 111. The inner upper end of the syringe cylinder 1 is installed with an annular ring 13. The lower end of the cylinder body 12 has a cylindrical ring 121.

An upper end of the syringe needle 2 is a needle tube 22 and the lower end is a needle 21. A periphery of the needle 21 has a protruding ring 211 and a lower end of the needle 21 has a hook seat 23. Two wedge rings 231 are arranged around the needle 21. A center of the hook seat 23 is a channel hole 230. The channel hole 230 penetrates through the needle 21 so as to communicate to the needle tube 22. The hook seat 23 is installed with a guide hole 232, as shown in the FIGS. 3 and 4.

A top of the push rod 3 has a push rod body 32 which is formed with a connecting block 321. The connecting block 321 is inserted into the combining hole 313 of a push rod cap 31, as shown in FIG. 5. The push rod cap 31 can be made of elastic material. A periphery of the push rod cap 31 has a positioning groove 312. A top center of the push rod cap 31 has an annular hook groove 311. The hook groove 311 has two stepped enlarged holes 3111. The rod body 32 has a through hole 320, as shown in the FIGS. 2, 3 and 5.

Thereby, the syringe needle 2 can pass through the positioning hole 110 of the syringe connecting seat 11 of the syringe cylinder 1. The positioning groove 111 in the positioning hole 110 is engaged with the protruding ring 211 of the needle 21. The guide hole 232 on the hook seat 23 of the syringe needle 2 is helpful to guide the injection liquid.

Thereby, the annular ring 13 at the upper end of the syringe cylinder 1 can be embedded into the hook groove 311 on the top surface of the push rod cap 31 when the push rod 3 moves upwards to the top end so as to prevent the injection liquid remained in the hook groove 311. The cylinder body 12 of the cylinder 1 has a cylindrical ring 121 which is engaged to the positioning groove 312 installed at the push rod cap 31 at the top of the push rod. Thus, when the push rod is drawn out, the cylinder body 12 will not be drawn out.

Figures 6, 7:
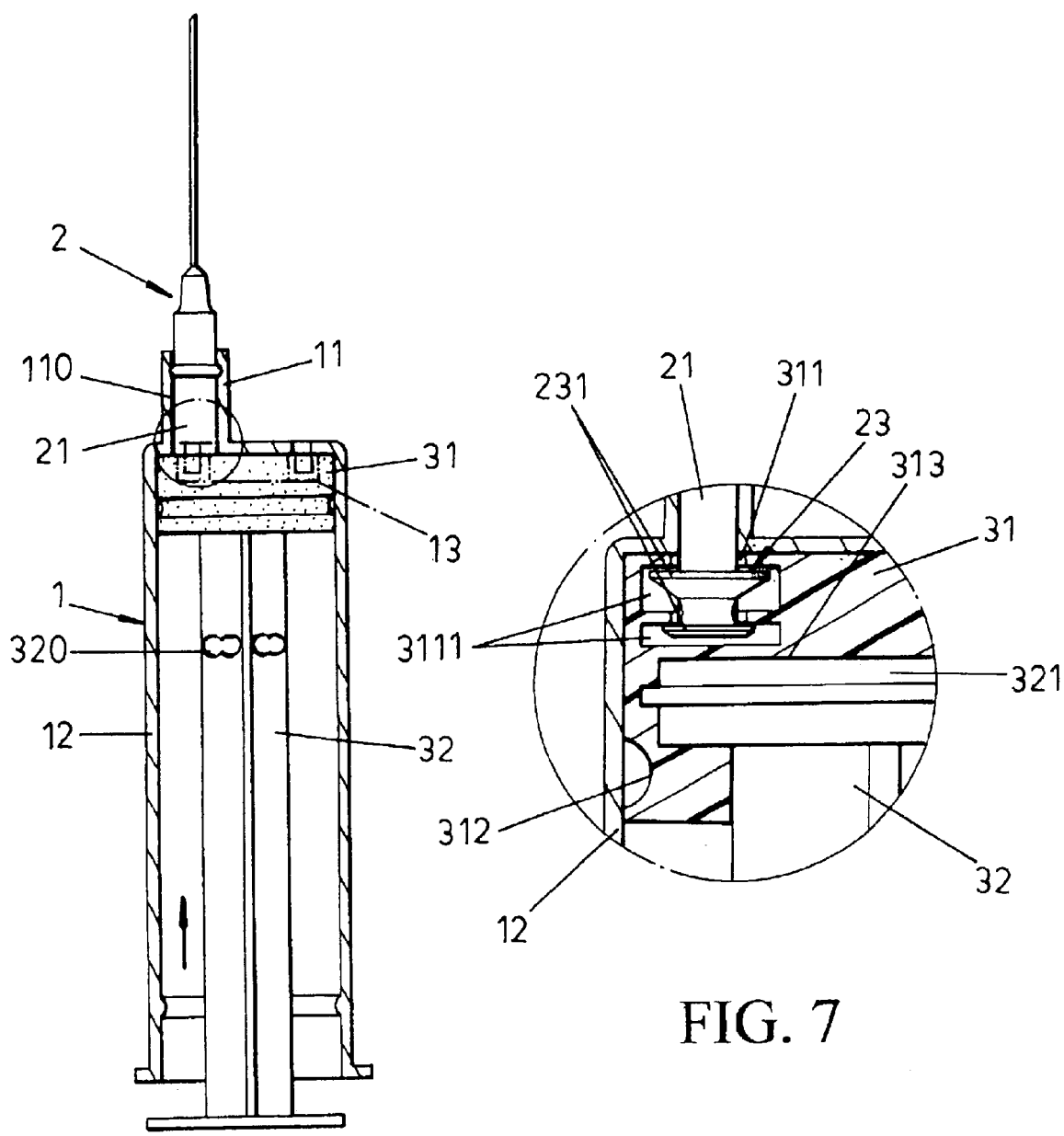
FIG. 6 is a partial structural view of the present invention.
FIG. 7 is a structural schematic view of the present invention.
Figures 8, 9:
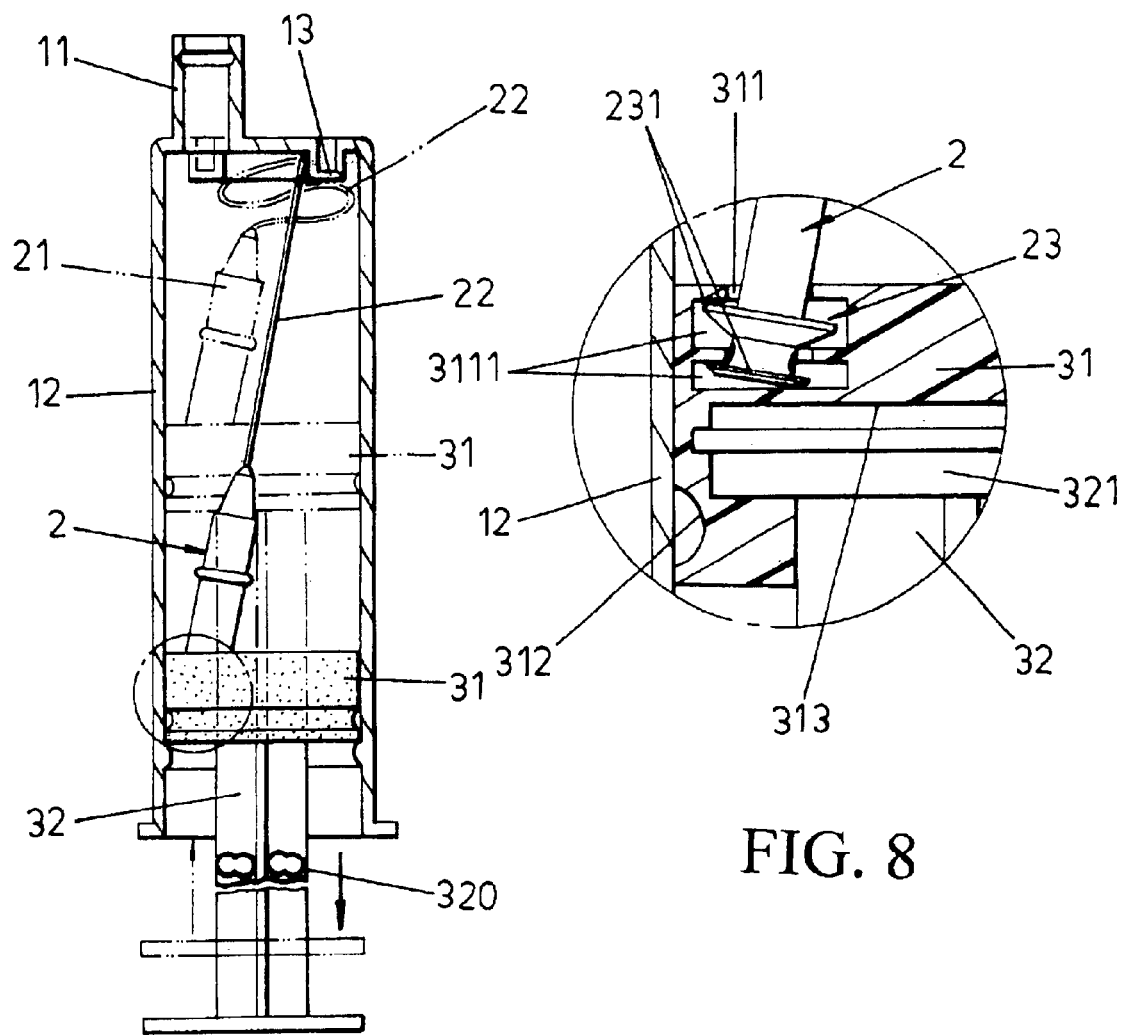
FIG. 8 is a partial structural schematic view of one embodiment of the present invention.
FIG. 9 shows one structural schematic view of one embodiment of the present invention.
Figure 10:
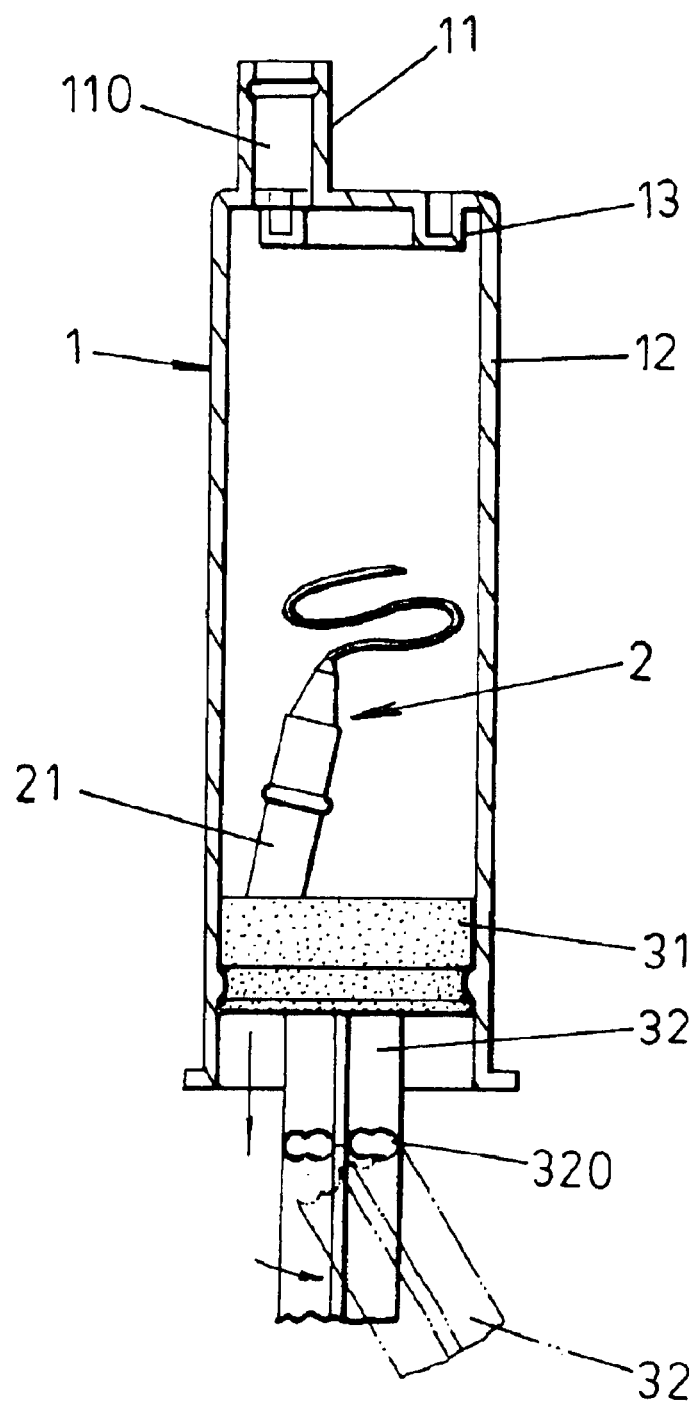
FIG. 10 is a schematic view of one embodiment of the present invention, where the present invention is pulled backwards.
Figures 11, 12:
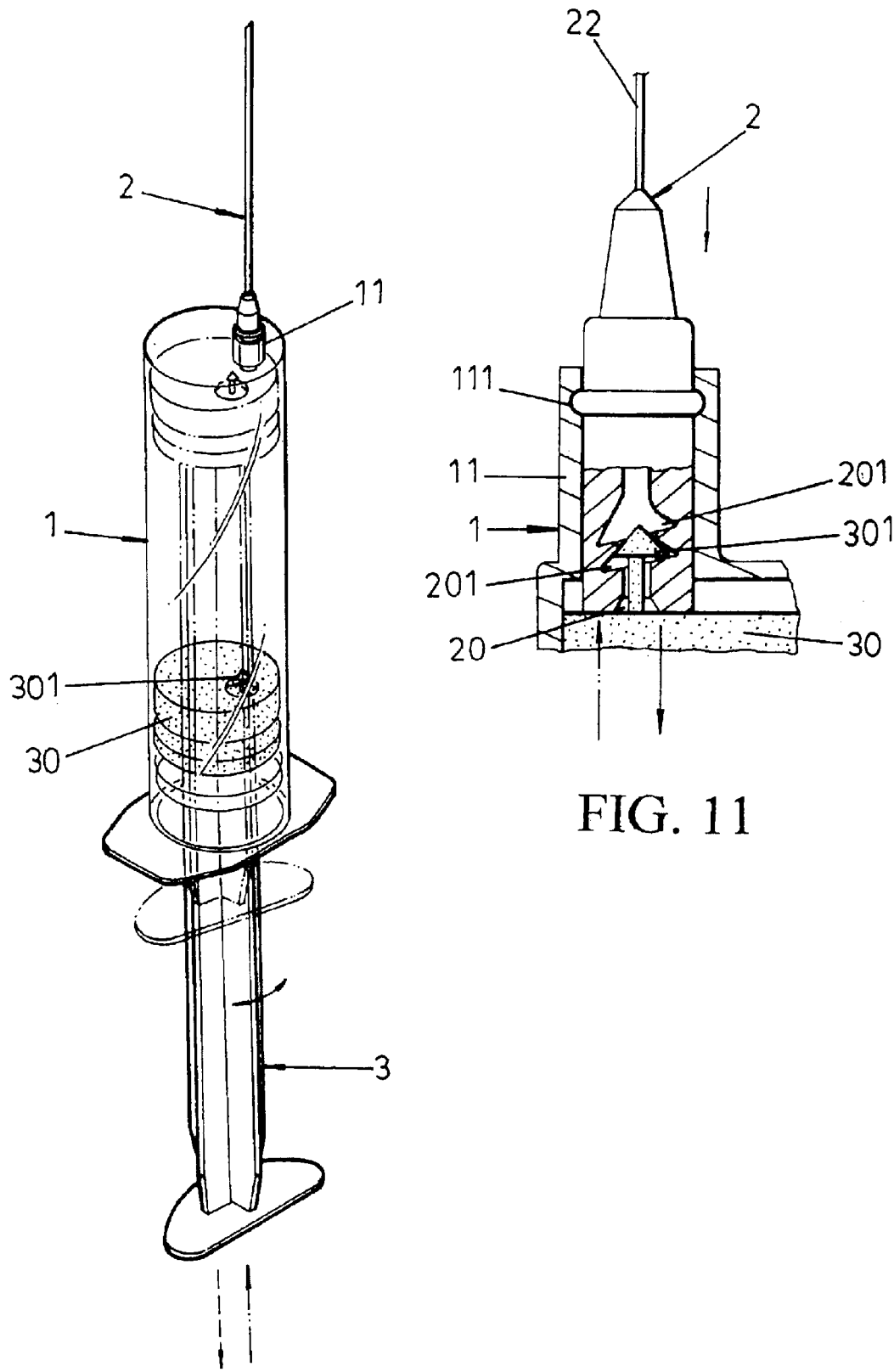
FIG. 11 is a structural schematic view of a prior art structure.
FIG. 12 is a partial schematic view of the prior art.

By above construction, the safety syringe cylinder can be formed. The retractable safety syringe cylinder of the present invention is used once for preventing from being infected. Referring to FIG. 3, the syringe cylinder 1 is full of injection liquid. By pushing the push rod 3, the liquid will flow through the channel hole 230 of the needle 2 and then is sent out form the syringe tube 22. By further pushing the push rod 3, after all the liquid has been sent out, the push rod cap 31 at the top of the push rod 3 exactly resists against the hole seat 23 of the needle 21. The annular hook groove 311 is installed at the top surface of the push rod cap 31. The hook seat 23 of the needle 21 is exactly inserted into the hook groove 311. The hook seat 23 does not shift from the annular hook groove 311 of the push rod cap 3 despite of the rotation and movement of the push rod 3. Referring to FIGS. 6 and 7, the hook seat 23 is inserted into the hook groove 311. By the engagement of the wedge rings 231 and the enlarged holes 3111, if the syringe needle 2 retracts, it will leave from the syringe connecting seat 11 to be within the cylinder body 12, as shown in the FIG. 9. By the wedge rings 231 to be loosely engaged with the enlarged holes 3111, although the syringe needle 2 can not leave from the syringe cylinder, but it can shift. With reference to FIG. 8, when the syringe needle 2 shifts to one side, the push rod can be pushed further. Then the syringe needle 2 will bent in the cylinder body 12. Then the push rod is retracted again, and thus the push rod body 32 can break through the through hole 320, as shown in FIG. 10, without piercing operator.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A safety syringe cylinder comprising a syringe cylinder, a syringe needle, a push rod; wherein an upper end of the syringe cylinder has a syringe connecting seat; and a center of the syringe connecting seat has a positioning groove;

an upper end of the syringe needle is a needle tube and a lower end thereof is a needle; a lower end of the needle has a hook seat; two wedge rings are arranged around the needle; a center of the hook seat is a channel hole; the channel hole penetrates through the needle so as to communicate with the needle tube;

a top of the push rod has a push rod body which is formed with a connecting block; the connecting block is inserted into the combining hole of a push rod cap; the push rod cap is made of elastic material; a periphery of the push rod cap has a positioning groove; a top center of the push rod cap has an annular hook groove; the hook groove has two stepped enlarged holes;

thereby, the syringe needle is combined with the positioning hole of the syringe connecting meat of the syringe cylinder; and push rod is inserted into the cylinder body of the syringe cylinder;

wherein an inner upper end of the syringe cylinder is installed with an annular ring; the annular ring is embedded into the hook groove on the top surface of the push rod cap when the push rod moves upwards to a top end of the syringe cylinder so as to prevent the injection liquid remained in the hook groove.

2. The safety syringe cylinder as claimed in claim 1, wherein the hook seat of the syringe needle has a guide hole for guiding the flow of syringe liquid.

3. The safety syringe cylinder as claimed in claim 1, wherein the push rod is formed with a through hole, thereby, the push rod can be broken for re-use or discard.

* * * * *